US008897458B2

(12) United States Patent
Parkins et al.

(10) Patent No.: US 8,897,458 B2
(45) Date of Patent: Nov. 25, 2014

(54) CONCHA-FITTING CUSTOM EARPLUG WITH FLEXIBLE SKIN AND FILLER MATERIAL

(75) Inventors: John W. Parkins, Ithaca, NY (US); Mark DeWilde, Ithaca, NY (US)

(73) Assignee: Red Tail Hawk Corporation, Ithaca, NY (US)

( * ) Notice: Subject to any disclaimer, the term of this patent is extended or adjusted under 35 U.S.C. 154(b) by 346 days.

(21) Appl. No.: 13/430,065

(22) Filed: Mar. 26, 2012

(65) Prior Publication Data

US 2012/0243701 A1 Sep. 27, 2012

Related U.S. Application Data

(60) Provisional application No. 61/467,711, filed on Mar. 25, 2011.

(51) Int. Cl.
| | | |
|---|---|---|
| *A61F 11/06* | (2006.01) | |
| *A61F 11/08* | (2006.01) | |
| *H04R 25/00* | (2006.01) | |
| *B29C 67/00* | (2006.01) | |

(52) U.S. Cl.
CPC ............... *A61F 11/08* (2013.01); *H04R 25/652* (2013.01); *H04R 25/658* (2013.01); *B29C 67/0059* (2013.01)
USPC ............................................................ 381/72

(58) Field of Classification Search
CPC ... A61F 11/06; A61F 11/08; A61F 2011/145; G10K 11/1178; H04R 1/1083; H04R 1/1008; H04R 25/60; H04R 25/65; H04R 25/652; H04R 2225/63; H04R 2225/021

USPC .......................................................... 381/72
See application file for complete search history.

(56) References Cited

U.S. PATENT DOCUMENTS

| | | | |
|---|---|---|---|
| 5,333,622 A * | 8/1994 | Casali et al. ................... | 128/864 |
| 5,631,965 A * | 5/1997 | Chang et al. ..................... | 381/72 |
| 6,022,311 A | 2/2000 | Juneau et al. | |
| 6,228,020 B1 | 5/2001 | Juneau et al. | |
| 6,254,526 B1 | 7/2001 | Juneau et al. | |
| 6,339,648 B1 | 1/2002 | McIntosh et al. | |
| 6,354,990 B1 | 3/2002 | Juneau et al. | |
| 6,425,398 B1 * | 7/2002 | Hirshfeld ....................... | 128/864 |
| 6,434,248 B1 | 8/2002 | Juneau et al. | |
| 6,438,244 B1 | 8/2002 | Juneau et al. | |
| 6,473,512 B1 | 10/2002 | Juneau et al. | |
| 6,533,062 B1 | 3/2003 | Widmer et al. | |
| 6,584,207 B1 | 6/2003 | Yoest et al. | |

(Continued)

OTHER PUBLICATIONS

Todd Fortune, PhD; Larry Humes, PhD; Robert Turner, PhD; Roger Juneau, BSME; and Edward Desporte, MS. "Clinical Evaluation of Silicone Soft Shell Technology", The Hearing Review, Aug. 2003.

(Continued)

*Primary Examiner* — Simon Sing
(74) *Attorney, Agent, or Firm* — Brown & Michaels, PC (57) ABSTRACT

An earplug which conforms to the concha of the ear and extends into the ear canal. The construction consists of a flexible outer skin with at least one filler material, preferably two or more materials of varying hardness, to form an essentially solid structure except for sound channels, or electronics packages, or other devices, parts and cavities that may be located within the flexible skin. The flexible skin can be fabricated using a rapid-prototyping printing process.

15 Claims, 5 Drawing Sheets

(56) References Cited

U.S. PATENT DOCUMENTS

| | | |
|---|---|---|
| 6,695,943 B2 | 2/2004 | Juneau et al. |
| 6,761,789 B2 | 7/2004 | Juneau et al. |
| 6,766,878 B2 | 7/2004 | Widmer et al. |
| 7,025,061 B2 | 4/2006 | Haussmann |
| 7,130,437 B2 | 10/2006 | Stonikas et al. |
| 7,217,335 B2 | 5/2007 | Juneau et al. |
| 7,574,917 B2 * | 8/2009 | Von Dach et al. ............. 73/646 |
| 7,875,223 B2 | 1/2011 | Masters |
| 8,054,985 B2 * | 11/2011 | Doty .............................. 381/72 |
| 8,107,638 B2 * | 1/2012 | Zwislocki ...................... 381/72 |
| 8,285,408 B2 * | 10/2012 | Schiller et al. .................. 700/98 |
| 2003/0029459 A1 * | 2/2003 | Tiemens ...................... 128/864 |
| 2003/0133583 A1 * | 7/2003 | Widmer et al. ............... 381/328 |
| 2005/0087195 A1 * | 4/2005 | Huang ........................... 128/864 |
| 2008/0314393 A1 * | 12/2008 | Purcell et al. ................. 128/865 |

OTHER PUBLICATIONS

Oliveira, Robert J., "The Active Ear", Journal of American Academy of Audiology, Dec. 1997, pp. 401-410.

\* cited by examiner

| LEGEND | |
|---|---|
| (1) shell = | ■ |
| (2) 1st filler = | ⋅⋅⋅⋅ |
| (3) 2nd filler = | ▓ |

| LEGEND | |
|---|---|
| (1) shell = | ▬ |
| (2) 1st filler = | · · · |
| (3) 2nd filler = | ▦ |
| (4) 3rd filler = | ⋯ |
| (21) electronics = | ╱ ╱ |

CONCHA-FITTING CUSTOM EARPLUG WITH FLEXIBLE SKIN AND FILLER MATERIAL

REFERENCE TO RELATED APPLICATIONS

This application claims one or more inventions which were disclosed in Provisional Application No. 61/467,711, filed Mar. 25, 2011, entitled "Concha-Fitting Custom Earplug with Flexible Skin and Filler Material". The benefit under 35 USC §119(e) of the United States provisional application is hereby claimed, and the aforementioned application is hereby incorporated herein by reference.

ACKNOWLEDGMENT OF GOVERNMENT SUPPORT

This invention was made with Government support under contract N68335-10-C-0329 with the United States Navy. The government has certain rights in the invention.

BACKGROUND OF THE INVENTION

1. Field of the Invention

The field of this invention is hearing protection, specifically in high noise environments where effective communications may also be needed.

2. Description of Related Art

There are numerous earplug devices currently patented, the majority of which are mass-produced designs based on soft elastomers or foam materials. They are placed in the ear canal and occupy positions up to but not generally past the second bend of the ear canal. Custom fitted ear plugs have also been designed and are commercially available as soft solid silicone plugs which are placed in the concha and outer ear canal, and as hard shell devices such as those described by Haussmann (U.S. Pat. No. 7,025,061) that reside in the same area. Recently, deep insertion custom solid silicone earplugs which extend through the second bend of the ear canal have been tested by the armed forces. These devices have been found to produce superior attenuation to other types due to their deep insertion up to and sometimes past the second bend of the ear canal (although comfort is an issue).

Virtually all custom hearing protectors have been designed and fabricated using the same technologies that are used to create hearing aids. For this reason, a brief discussion of hearing aids is useful. All hearing aids receive sound via a microphone, amplify the signal produced, and then drive a speaker which is configured so that the sound produced is directed to the eardrum. There are a number of hearing aid types. Accepted industry type names include "In-The-Ear" (ITE), "In-the-canal" (ITC), "Completely-In-Canal" (CIC), and "Behind-the-Ear" (BTE). Each device name denotes a distinct and broadly accepted definition of geometry. ITE devices fit in the outer ear concha and extend only minimally into the ear canal. These devices are visible looking into the ear, and often visible when facing the person from the front. ITC devices are smaller, and fill only the innermost portion of the external ear, and the outermost portion of the ear canal and opening of the canal. They are visible looking into the ear, but very little from the front. CIC devices are generally fitted deep into the ear canal and may be invisible altogether even when looking into the ear. BTE devices are large curved devices that fit behind the ear and provide a sound tube which passes over the top of the ear and into the ear canal where an eartip is located. ITE, CIC, and ITC hearing aids typically use hollow shells with the electronics and transducers fitted inside them.

In addition, special molds have been used to produce solid plugs, and soft flexible hearing aids as well as earmolds for BTE hearing aids.

The primary difference between a hearing device that is a hearing aid and a device that is a hearing protector lies in the differing goals of amplification vs. attenuation. The technologies used to create custom devices of either type are similar and share many common elements. Both types of devices begin by acquiring an impression of the outer ear and ear canal where the device is intended to reside. This is typically done by injecting a fast curing material into the ear canal and concha. This impression can be processed into a device using the traditional invest and cast methods which are widely described in the literature, or using a digital approach wherein the impression is converted into a 3D mathematical representation, often by using a laser scanner, and manipulated to become a device design using various specialized software packages. The device or a set of molds for the device are then created using 3D printing, also known as Rapid Prototyping. These systems employ Stereolithography (SLA), Selective laser Sintering (SLS), jet droplet deposition, or other methods. In the case of hard earshell based devices, the shell can be printed directly from an otoplastic. In the case of a cast device, the mold may be printed directly, and the device material cast into it. Once cured, the mold is removed.

SUMMARY OF THE INVENTION

A custom fitted hearing protection earplug which conforms to the concha of the ear and extends into the ear canal. The construction consists of a custom-shaped flexible shell with filler material (preferably two or more) to form an essentially solid structure except for sound channels, or electronics packages, or other devices, parts and cavities that may be located within the flexible shell. The flexible skin can be fabricated using a rapid-prototyping printing process. The advantages of this structure, manufacture technique, and extensions to include communications enhancements are discussed.

DETAILED DESCRIPTION OF THE INVENTION

Figure 7:
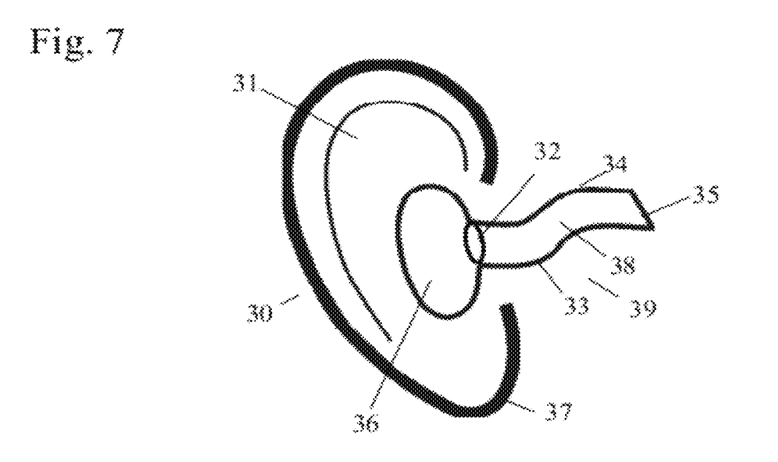
FIG. 7 shows the geometry of a human ear.

FIG. 7 shows the geometry of a human ear relevant to the invention. The external ear 30 comprises a pinna 31, a concha 36, an earlobe 37, and an ear canal opening 32. The middle ear 39 comprises the ear canal 38, which starts at the ear canal opening 32 and leads inward to the eardrum 35, passing through a first bend 33 and a second bend 34.

Figure 1:
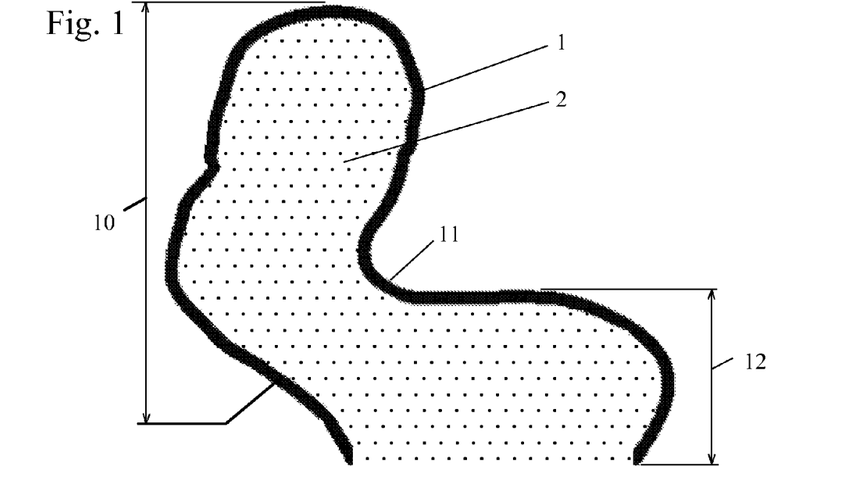
FIG. 1 shows an earplug with filler material, and flexible shell.

FIG. 1 shows an embodiment of a passive ear plug according to the present invention. The invention is an in-the-ear (ITE) device having a portion 12 that resides in the concha, up to the opening 11 of the ear canal, and a portion 10 that resides in the ear canal and can extend up to and through the second bend of the ear canal.

The earplug is a hybrid of a shell-type device and a solid plug type of device, being made of a flexible shell 1 filled with a filler material 2. This hybrid device, unlike a CIC device, is easy to insert and take out because it extends into the concha region which is easy to access. It is no more conspicuous than an ITE device, but offers much greater sound attenuation than ITE or ITC devices. Unlike a simple concha-resident hearing protector as is described by Haussman '061, the portions 10 that reside deeply in the ear canal prevent small movement of the concha portion 12 from breaking the acoustic seal and permitting sound to enter.

The shell 1 can be designed digitally using a commercial earshell design software package, and can be 3D printed in a flexible otoplastic material on a rapid prototyping (RP) machine such as the Desktop Digital Shell Printer (DDSP) from Envisiontec. The wall thickness of the printed shell 1 determines its flexibility. In areas where high flexibility is desired, the shell 1 wall thickness can be minimized. Conversely, in areas where stiffness is required, the shell wall thickness can be increased.

Figure 8:
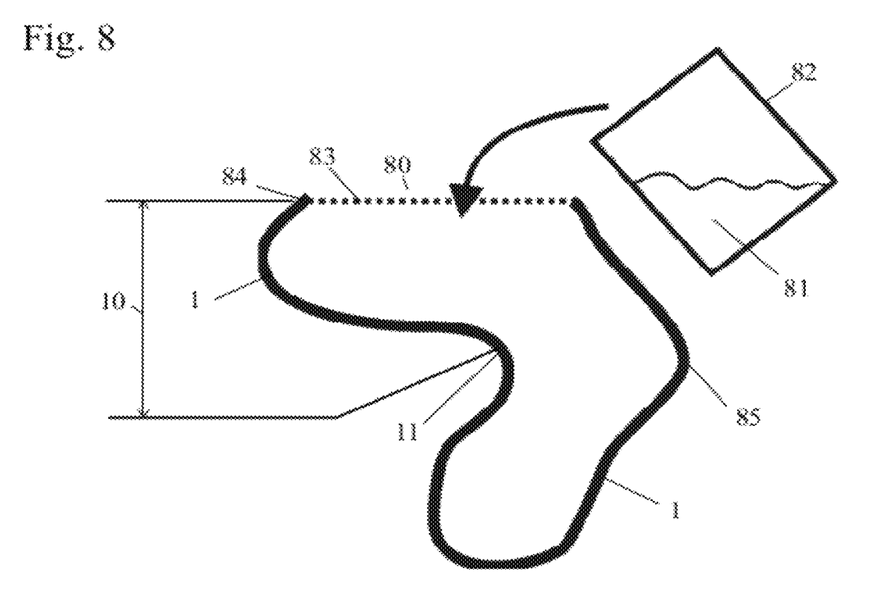
FIG. 8 illustrates a method of making an earplug of FIG. 1.

FIG. 8 shows the orientation of a flexible shell 1 ready for pouring filler material 2. Once the flexible shell 1 is printed, any interior supports needed for the 3D printing process are removed from the shell 1 and the part is cleaned of any RP resin remaining. Next, the shell 1 is positioned in a fixture (not shown) with the open base 80 pointing upward. The shell 1 is angled so that the surface of a liquid material poured into it will lie in the desired plane. As shown in FIG. 8, when curable material 81 in container 82 is poured into flexible skin 1 completely, a flat surface 83 will result at the top 84 of the earplug in the concha region 10.

Once the curable material 81 is cured, any final finishing, such as trimming any exterior supports and/or buffing of the flexible shell 1, is performed.

FIG. 1 shows an earplug prepared according to this method, using a single soft flexible material as the filler material 2.

An advantage of this design is that the shell 1 can be fabricated with a material that provides a smoother finish compared to the filler material 2 or is easier to buff or smooth compared to filler material 2. For example, otoplastic urethane material can be very strong and flexible, but it is difficult to produce a solid earplug with a smooth finish because the natural bubbles in the urethane are difficult to eliminate. If the flexible shell 1 is filled with the urethane, the earplug benefits from the surface finish of the otoplastic shell 1 and the flexibility and toughness of the urethane filler 2.

The filler materials 2 are preferred to be biologically compatible but not required to be since they do not contact skin due to the flexible otoplastic shell 1. By the same mechanism, the materials used for filling the shell are protected from cerumen, perspiration and other bodily fluids so that they do not break down due to contact with them and lose their desirable properties. This relaxation of the biologic compatibility requirement on the fillers widens the range of materials usable for the application.

The filler materials are also chosen to have adhesive properties so that bonding to the shell 1 and to each other is assured. A separate bonding agent is not necessary in this invention. The materials could be polymers, waxes, gels, foams, or other materials with suitable mechanical and acoustic properties and also include silicones and urethanes. Additionally, the earplug may be coated with a flexible material, such as silicone, by dipping, brushing, or spraying on the material, to form a smoother finish.

Figure 2:
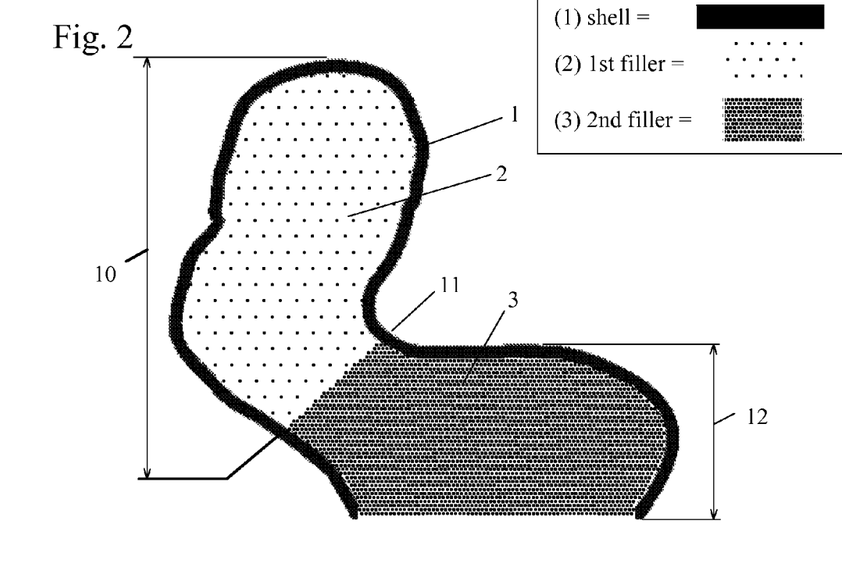
FIG. 2 shows an earplug with two filler materials, and flexible shell
Figure 9A:
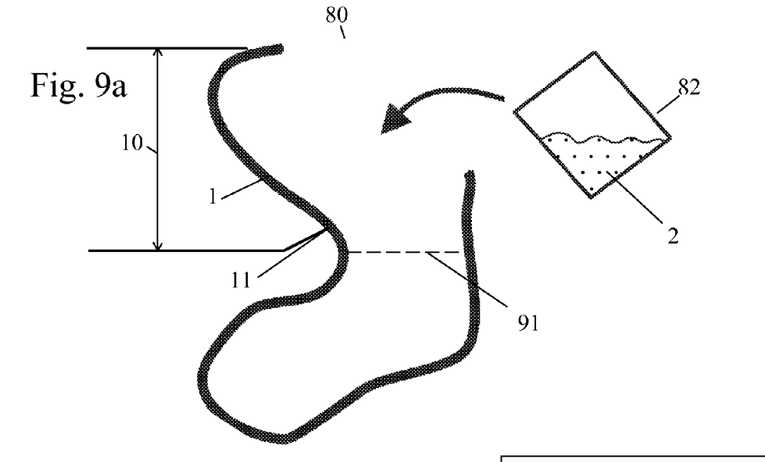
FIGS. 9a-9b illustrate a method of making an earplug of FIG. 2
Figure 9B:
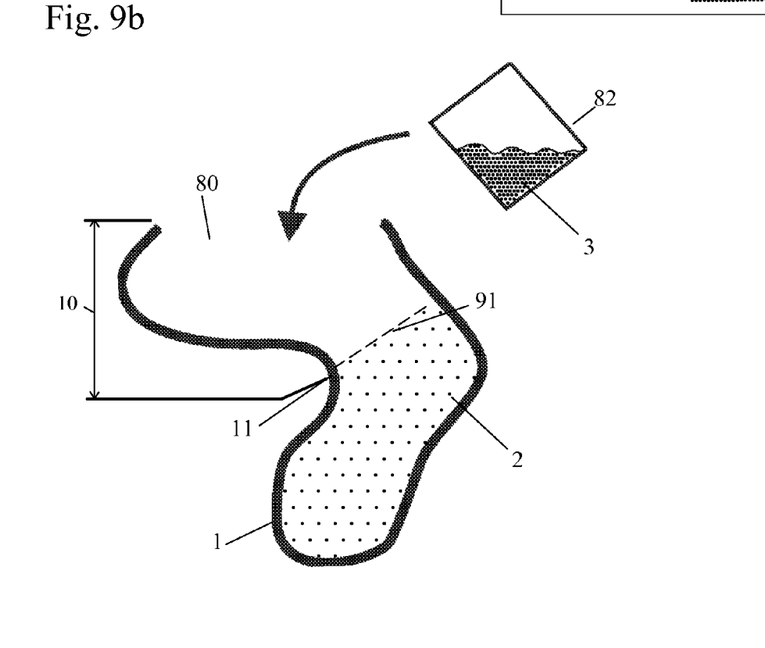

FIG. 2 shows a two-part embodiment of a passive ear plug, similar to the plug of FIG. 1, being an in-the-ear (ITE) device having a portion 12 that resides in the concha, up to the opening 11 of the ear canal, and a portion 10 that resides in the ear canal and can extend up to and through the second bend of the ear canal. FIGS. 9a to 9b illustrate the method of making the earplug of FIG. 2.

The shell 1 can be formed by 3D printing, as discussed above, using an RP machine. Once printed, any interior supports needed for the printing process are removed from the shell 1 and the part is cleaned of any RP resin remaining.

Next (FIG. 9a), the shell 1 is positioned in a fixture with the open base 80 pointing upward. The shell 1 is angled so that the surface of a liquid poured into it will lie in the desired internal plane 91, typically the opening of the ear canal 11. A relatively soft curable material 2 is then poured from container 82 into the internal cavity of the shell 1 and permitted to cure either partially or fully.

Next (FIG. 9b), the shell 1 is repositioned so that the next poured layer 3 surface 92 will be in the desired plane, typically at the top 80 of the concha region 10. The fill material 3 is then poured in from the container 82 and permitted to cure. Fill material 3 cures to form a relatively hard material.

Figure 3:
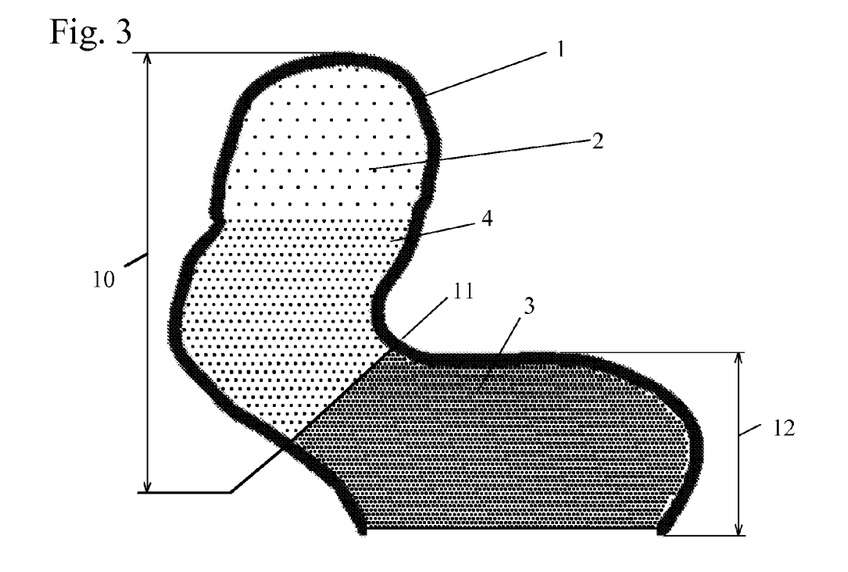
FIG. 3 shows an earplug with three filler materials, and flexible shell.

The number of different filler materials is not limited to two. FIG. 3 shows a three-material filled plug. In this case, a very soft material 2 may be used for the tip section, to maximize comfort. A medium soft material 4 is used for the mid section to provide adequate stiffness for insertion without excess deformation, but still to be able to flex to allow easier insertion past the bends of the ear canal. A relatively hard material 3 is used in the concha section 12 as was done for the two-part plug of FIG. 2. The filler materials could be three different durometers of urethane or silicone, for example.

If an internal element such as a vent tube is desired, it may be installed as a separate component in the shell and held in position during the casting process by a wire or fixture before the polymeric material is poured. Alternately, using a digital design and printing process it is possible to incorporate the element into the plug design and then print it in the same material and at the same time as the flexible shell. When the casting occurs, the casting material will encapsulate the element in either case. Vent tubes, sound tubes, cavities to modify flexibility of the device locally, resonators, and wax guards may all be added.

Figure 4:
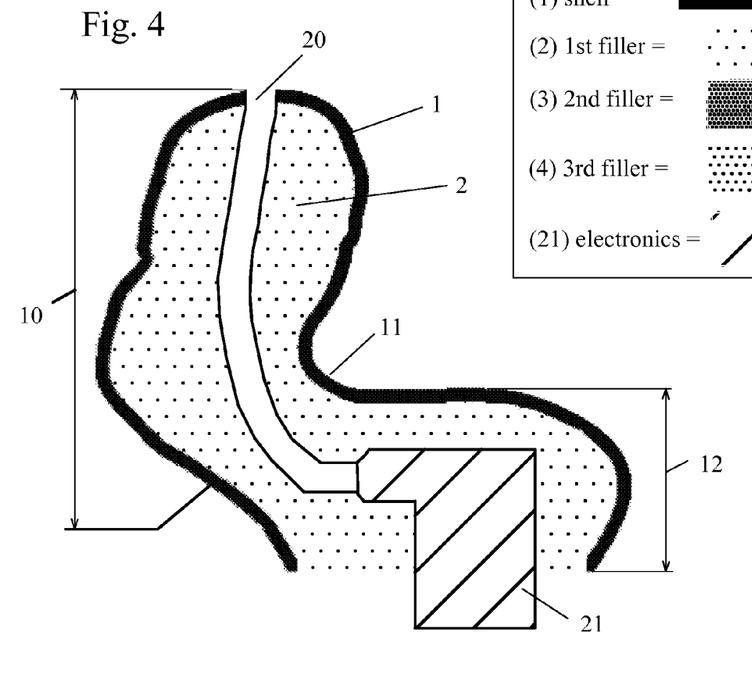
FIG. 4 shows an earplug with filler material, flexible shell and electronics package.
Figure 5:
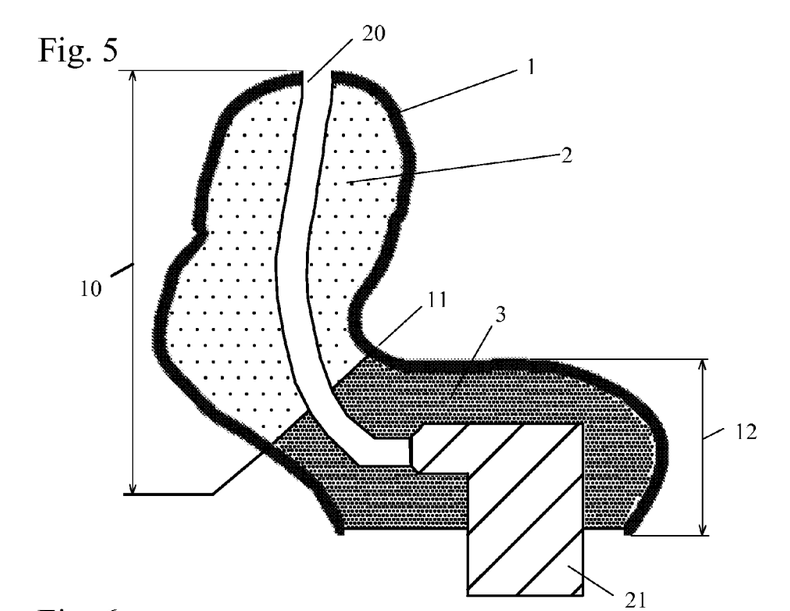
FIG. 5 shows an earplug with two filler materials, flexible shell and electronics package.
Figure 6:
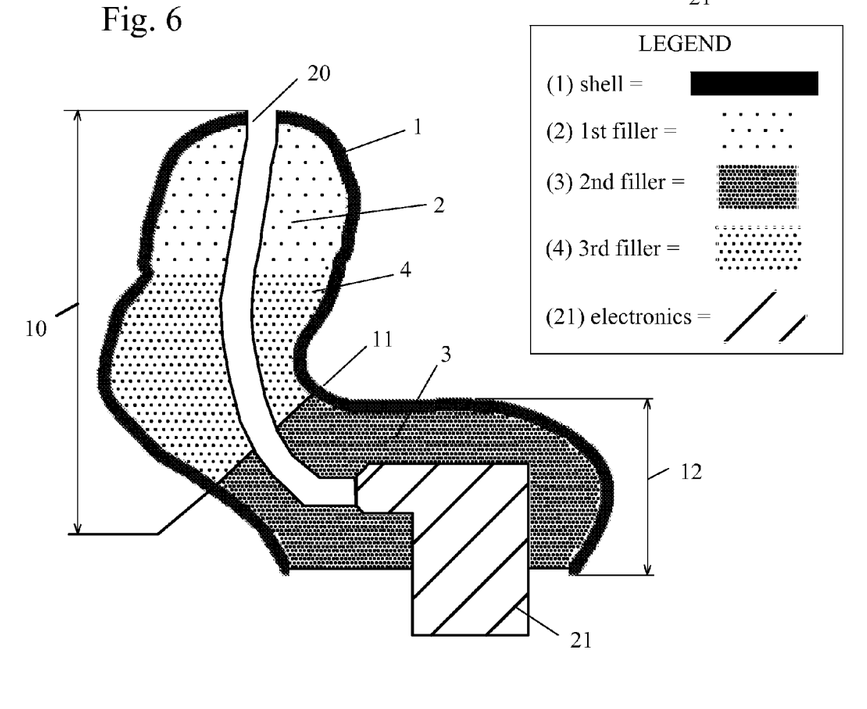
FIG. 6 shows an earplug with three filler materials, flexible shell and electronics package.

FIGS. 4 through 6 show earplugs having active components, in embodiments corresponding to the one-, two- and three-material embodiments shown in FIGS. 1 through 3, respectively. In these figures, an active component such as electronics package 21 is shown connected to a sound tube 20 which leads from the package 21 to an opening for the sound to be conducted into the user's ear at an end of the ear canal portion 10 of the earplug.

In an earplug having active components, such as transducers and electronics packages 21, the active components are placed in the concha region 12 of the shell 1 and encapsulated during the pouring of the materials. If multiple materials are used, it is advantageous for the material 3 used in the concha region 12 to be relatively hard. Thus, it will more securely capture electronics and/or transducers. Placing such components in the concha portion 12 instead of in the ear canal portion 10 of the device provides great ruggedness and protection of those components if they are embedded and encapsulated in hard material.

If the components are embedded in rigid material, they do not require a support or mounting structure such as a faceplate, which is commonly found in hearing aids, and adds cost to the earplug. Since the components are at least partially surrounded with encapsulating material, adhesives or separate bonding agents are not necessary to assure they remain firmly attached and in place.

Unlike devices built with only soft polymeric materials, in the multi-material embodiment of FIGS. 5 and 6, the soft filler material 2 is neither bonded to nor encapsulates the electronic components 21. Because of this, no special strain relieving or supportive elements are needed to protect wiring, component integrity and alignment, or sound passages.

A good example of an application in which the structure of FIGS. 4-6 would be useful would be adding radio or other communications capability (wired or wireless) to the earplugs. This affords hearing protection while reducing the interference of high ambient noise levels with desired communications transmissions.

There are several elements which should be noted in FIGS. 5 and 6.

First, the flexible shell 1 does not directly support the electronics package 21, rather the electronics package 21 is supported and protected via encapsulation in rigid material 3 and does not require additional elements such as faceplates and support structures. Second, the custom shaped flexible outer shell 1 remains a permanent part of the finished device, and serves also as the mold for the inner filling and encapsulating materials 2, 3 and 4. The ruggedness imparted by this geometry is particularly desirable in hearing protective devices worn in industrial, military, and other harsh environments where they will receive rough handling, be dropped or exposed to impacts.

While FIGS. 2, 3, 5 and 6 all illustrate the hard material ending at the opening of the ear canal 11, there is no requirement to do so. Hard materials may extend into the ear canal through the first bend of the canal since flexing of the ear canal between the concha and first bend is minimal. In some number of individuals, it has been found that a rigid plug in this region has a lowered tendency to move and cause irritation of the ear canal. The versatility of the device filling levels permits the construction to accommodate these individuals as well as those who prefer a longer flexible section.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. An earplug for an ear having an ear canal and a concha region, comprising:
    a flexible outer skin formed to fit in the ear, having a hollow interior, a portion formed for insertion into the ear canal, and a portion fitting in the concha region, wherein a thickness of the flexible outer skin varies, such that the skin of the earplug has greater or lesser stiffness in different sections of the ear canal; and
    a filler material substantially filling the interior of the skin, comprising at least one soft material in the portion of the outer skin for insertion into the ear canal.

2. The earplug of claim 1, wherein the outer skin comprises a material custom formed to fit a specific user using rapid prototyping technology.

3. The earplug of claim 1, wherein the filler material comprises a plurality of materials.

4. The earplug of claim 3, wherein the plurality of materials comprises the at least one soft material in a portion of the interior of the outer skin for insertion to the region of a first bend of the ear canal, and a relatively harder material in the portion of the outer skin fitting in the concha region.

5. The earplug of claim 4, wherein the plurality of materials further comprises a medium material between the soft material and the relatively harder material, the medium material having a hardness intermediate between the soft material and the relatively harder material.

6. The earplug of claim 1, wherein the filler material is selected from a group consisting of polymers, waxes, foams, gels, silicones and urethanes.

7. The earplug of claim 1, further comprising an active component at least partially encapsulated in the filler material in the portion of the outer skin fitting in the concha region.

8. The earplug of claim 7, further comprising a sound tube located in the interior of the earplug, having a first end acoustically coupled to the active component and a second end in the portion of the earplug for insertion into the ear canal.

9. The earplug of claim 8, wherein the second end of the sound tube is coupled to an opening in the flexible outer skin in the portion of the earplug for insertion into the ear canal.

10. The earplug of claim 7, wherein the material encapsulating the active component is a rigid material.

11. The earplug of claim 7, wherein the active component is a sound transducer.

12. A method of making a custom earplug for fitting in a user's ear, the ear having an ear canal and a concha region, the earplug comprising a flexible outer skin formed to fit in the ear, having a hollow interior, a portion formed for insertion into the ear canal, and a portion fitting in the concha region and a filler material substantially filling the interior of the outer skin, comprising at least one soft material in the portion of the skin for insertion into the ear canal; the method comprising the steps of:
    a) printing the flexible outer skin using a rapid prototyping machine from a digital image of the ear canal and concha region to form the flexible outer skin into the shape of the user's ear canal and concha region, wherein a thickness of the flexible outer skin varies, such that the skin of the earplug has greater or lesser stiffness in different sections of the ear canal;
    b) orienting the flexible outer skin with an open base pointing upward, the outer skin being angled such that a desired fill surface is horizontal, the desired fill surface being located at least at a level corresponding with an opening of the ear canal;
    c) pouring a soft filler material into the open base of the flexible outer skin to fill the skin to the desired fill surface; and
    d) allowing the filler material to cure.

13. The method of claim 12, further comprising the steps of:
    e) orienting the flexible outer skin such that the open base is horizontal;
    f) pouring a second filler material into the open base of the flexible outer skin which is harder than the soft filler material poured in step (c), to fill the skin up to a level near the open base of the flexible outer skin; and
    g) allowing the second filler material to cure.

14. The method of claim 13, further comprising the steps, between steps (d) and (e), of:
    i) orienting the flexible outer skin, angled such that an intermediate desired fill surface is horizontal, the intermediate fill surface being located between the desired fill surface of step (b) and the level of step (f);

ii) pouring an intermediate filler material into the open base of the flexible outer skin which is harder than the soft filler material poured in step (c) and softer than the second filler material poured in step (f), to fill the skin to the intermediate desired fill surface; and iii) allowing the intermediate filler material to cure.

15. The method of claim 12, further comprising the step of buffing the earplug.

\* \* \* \* \*